United States Patent
Buffa et al.

(10) Patent No.: US 6,239,290 B1
(45) Date of Patent: May 29, 2001

(54) SILICONE FUNCTIONALIZED SORBITAN ESTERS

(76) Inventors: Charles W. Buffa, 510 E. 31st St., Paterson, NJ (US) 07504; Anthony J. O'Lenick, Jr., 2170 Luke Edwards Rd., Dacula, GA (US) 30019

( * ) Notice: Subject to any disclaimer, the term of this patent is extended or adjusted under 35 U.S.C. 154(b) by 0 days.

(21) Appl. No.: 09/657,561

(22) Filed: Sep. 8, 2000

(51) Int. Cl.$^7$ .............................. C07F 7/08; C07D 303/02
(52) U.S. Cl. ................................................ 549/214
(58) Field of Search ............................................. 549/214

(56) References Cited

U.S. PATENT DOCUMENTS

| | | |
|---|---|---|
| 5,292,847 | 3/1994 | O'Lenick . |
| 6,013,813 | 1/2000 | O'Lenick . |
| 6,069,259 * | 5/2000 | Crivello ................................ 549/214 |
| 6,096,903 * | 8/2000 | Moszner et al. ...................... 549/214 |
| 6,121,463 * | 9/2000 | Parker et al. ..................... 549/214 X |

* cited by examiner

Primary Examiner—Paul F. Shaver

(57) ABSTRACT

The present invention deals with novel emulsifiers that have excellent feel on the skin are essentially non-irritating to the eyes and the skin and can be used to make unique silicone in water and water in silicone emulsions. The compounds are esters made by the reaction of sorbitol and carboxy functionalized silicone compounds. The introduction of the silicone portion of the molecule into the compounds of the present invention results in improved emulsification efficiency of silicone oils, improved oxidative stability and improved liquidity of the sorbitan esters as well as an outstanding skin feel of emulsions made with said emulsifiers.

15 Claims, No Drawings

SILICONE FUNCTIONALIZED SORBITAN ESTERS

BACKGROUND OF THE INVENTION

1. Field of the Invention

The present invention deals with novel emulsifiers that have excellent feel on the skin are essentially non-irritating to the eyes and skin and can be used to make unique silicone in water and water in silicone emulsions. The compounds are esters made by the reaction of sorbitol and carboxy functionalized silicone compounds. The introduction of the silicone portion of the molecule into the compounds of the present invention results in improved emulsification efficiency of silicone oils, improved oxidative stability and improved liquidity of the sorbitan esters as well as an outstanding skin feel of emulsions made with said emulsifiers. Emulsions made with standard sorbitan esters have a tendency to be sticky and cosmetically unappealing.

2. Description of the Art Practices

U.S. Pat. No. 5,296,625 to O'Lenick et al discloses silicone alkoxylated ester carboxylates. These carboxylates are not suitable to make sorbitan esters, since the linkage group from silicone to the carboxyl group is through an ester group. This group will hydrolyze in the presence of acid or base, and will transesterify if the attempt to react it with sorbitol is made.

Sorbitan esters have likewise been known for years. U.S. Pat. No. 2,322,821 describes the chemistry.

U.S. Pat. No. 6,013,813 issued Jan. 11, 2000 discloses guerbet based sorbitan esters. The guerbet gives improved oxidative stability over standard sorbitan esters, but does not address skin feel and the ability to provide very efficient emulsifiers for silicone oil.

U.S. Pat. No. 5,292,847 incorporated herein by reference issued in March 1994 discloses carboxy silicone alkoxylates. These carboxy silicones are raw materials in the preparation of the compounds of the present invention.

THE INVENTION

This invention relates to the use of a series of silicone functionalized sorbitan esters. The esters are made by the reaction of a silicone carboxylate and a sorbitol to make a new series of sorbitan esters.

Esters are a class of compounds which find applications in many diverse segments of the chemical industry. One of the problems which is encountered using non-branched fatty acids to make sorbitol based esters is the fact that the resulting products are dark in color and possess a mal odor. It is very desirable, particularly in cosmetic applications to have products that are light in color and free of bad odors.

The specific structure of the esters of the present invention determines the functional attributes of the product, including odor, color, emulsification and liquidity. The introduction of silicone into the backbone results in unexpectedly efficient emulsifiers for silicone, and emulsions with a cosmetically elegant skin feel.

DETAILED DESCRIPTION OF THE INVENTION

The compounds of the current invention are specific branched esters conforming to the following structure;

Sorbitan Mono Silicone Esters $$\text{HO}-\text{CH}-\text{CH}-\text{OH}$$
$$\quad\quad\ \ \text{CH}_2\ \ \text{CH}-\text{CH}-\text{CH}_2-\text{R}$$
$$\quad\quad\quad\ \ \backslash/\quad\quad\ \ |$$
$$\quad\quad\quad\ \ \text{O}\quad\quad\ \ \text{OH}$$

wherein;

R is $$\text{A}-\underset{\underset{\text{Me}}{|}}{\overset{\overset{\text{Me}}{|}}{\text{Si}}}-\text{O}-\left[\underset{\underset{\text{Me}}{|}}{\overset{\overset{\text{Me}}{|}}{\text{Si}}}-\text{O}\right]_m-\left[\underset{\underset{\text{Q}}{|}}{\overset{\overset{\text{Me}}{|}}{\text{Si}}}-\text{O}\right]_n-\underset{\underset{\text{Me}}{|}}{\overset{\overset{\text{Me}}{|}}{\text{Si}}}-\text{A}$$

wherein;

Me is methyl;

Q is a —$(CH_2)_c$—C(O)O—;

c is an integer ranging from 3 to 17;

A is either Me— or —Q— m is an integer ranging from 1 to 200;

n is an integer ranging 0 to 10 when A is —Q—, and an integer ranging from 1 to 10 when A is Me;

Sorbitan Di Silicone Ester $$\text{HO}-\text{CH}-\text{CH}-\text{R}$$
$$\quad\quad\ \ \text{CH}_2\ \ \text{CH}-\text{CH}-\text{CH}_2-\text{R}$$
$$\quad\quad\quad\ \ \backslash/\quad\quad\ \ |$$
$$\quad\quad\quad\ \ \text{O}\quad\quad\ \ \text{OH}$$

wherein;

R is $$\text{A}-\underset{\underset{\text{Me}}{|}}{\overset{\overset{\text{Me}}{|}}{\text{Si}}}-\text{O}-\left[\underset{\underset{\text{Me}}{|}}{\overset{\overset{\text{Me}}{|}}{\text{Si}}}-\text{O}\right]_m-\left[\underset{\underset{\text{Q}}{|}}{\overset{\overset{\text{Me}}{|}}{\text{Si}}}-\text{O}\right]_n-\underset{\underset{\text{Me}}{|}}{\overset{\overset{\text{Me}}{|}}{\text{Si}}}-\text{A}$$

wherein;

Me is methyl;

Q is a —$(CH_2)_c$—C(O)O—;

c is an integer ranging from 3 to 17;

A is either Me— or —Q— m is an integer ranging from 1 to 200;

n is an integer ranging 0 to 10 when A is —Q—, and an integer ranging from 1 to 10 when A is Me.

Sorbitan Tri-Silicone Ester

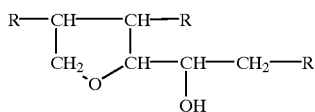

wherein;

R is

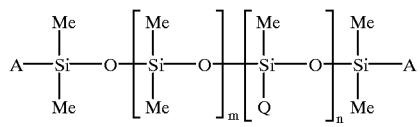

wherein;

Me is methyl;

Q is a —$(CH_2)_c$—C(O)O—;

c is an integer ranging from 3 to 17;

A is either Me— or —Q— m is an integer ranging from 1 to 200;

n is an integer ranging 0 to 10 when A is —Q—, and an integer ranging from 1 to 10 when A is Me;

It should be clearly understood that when the number of carboxyl groups is greater than 1, (that is when n is greater than 1) a polymeric crosslinkes species results. These polymeric structures do not penetrate the skin and are very mild.

Preferred Embodiment

Sorbitan mono-silicone Esters

In a preferred embodiment c is 10.

In another preferred embodiment n is an integer ranging from 2 to 10.

In another preferred embodiment c is 17.

In another preferred embodiment m is 10.

Sorbitan di-silicone Esters

In preferred embodiment c is 10.

In another preferred embodiment n is an integer ranging from 2 to 10.

In another preferred embodiment c is 17.

In another preferred embodiment m is 10.

Sorbitan tri-silicone Esters

In a preferred embodiment c is 10.

In another preferred embodiment n is an integer ranging from 2 to 10.

In another preferred embodiment c is 17.

In another preferred embodiment m is 10.

EXAMPLES

RAW MATERIALS

Carboxy Functionalized Silicone Compounds

Many manufacturers offer a series of carboxy functionalized silicone compounds suitable for use as raw materials in the preparation of the esters of the present invention. These materials are marketed under the many trade names. Siltech Inc, and Dow Corning.

The preferred method of placing this type of reactive carboxy group into the silicone polymer is by the reaction of silianic hydrogen containing polymer with a terminal unsaturated carboxylate. This technology is well known to those skilled in the art.

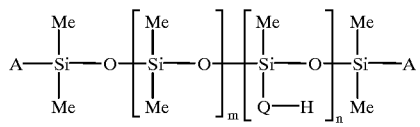

wherein;

Me is methyl;

Q is $(CH_2)_c$—C(O)—O—;

c is an integer from 3 to 17;

A is methyl;

m is an integer ranging from 1 to 200;

n is an integer ranging 0 to 10 when A is —Q—$R^1$, and an inter ranging from 1 to 10 when A is R;

| Example | Name | c | n | m |
|---|---|---|---|---|
| 1 | Siltech C 1000 | 10 | 3 | 15 |
| 2 | Siltech C 1100 | 10 | 1 | 20 |
| 3 | Siltech C 1200 | 3 | 4 | 50 |
| 4 | Siltech C 1300 | 3 | 2 | 200 |
| 5 | Siltech C 1400 | 4 | 1 | 29 |
| 6 | Siltech C 1500 | 17 | 3 | 1 |
| 7 | Siltech C 1600 | 17 | 4 | 150 |
| 8 | Siltech C 1700 | 4 | 10 | 55 |

Terminal Substituted Carboxy Functionalized Silicone

Terminal substituted carboxy functionalized silicone compounds are well known and are marketed in the trade under many names.

The preferred method of placing this type of carboxyl group into the silicone polymer is by the reaction of terminal silianic hydrogen containing polymer with a terminal vinyl containing carboxy compound.

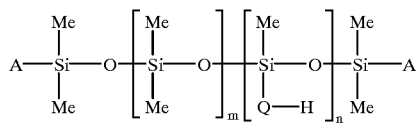

wherein;

Me is methyl;

Q is $(CH_2)_c$—C(O)—O—;

c is an integer from 3 to 17;

n is 0;

A is —Q—H;

| Example | Name | c | m |
|---|---|---|---|
| 9 | Siltech CT 701 | 10 | 1 |
| 10 | Siltech CT 706 | 3 | 200 |
| 11 | Siltech CT 710 | 17 | 50 |
| 12 | Siltech CT 750 | 10 | 100 |
| 13 | Siltech CT 790 | 3 | 150 |

Sorbitol

Sorbitol six carbon poly-hydroxy compound conforming to the following structure:

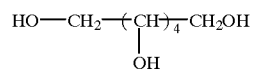

Sorbitol is an item of commerce and is generally sold as a 70% solution in water. The molecule undergoes a reaction under base conditions to cyclize. The optimum cyclization conditions are using KOH at a concentration of between 0.1 and 1.0%. Many ring containing compounds result. Details of the type of compounds produced are outlined in U.S. Pat. No. 2,322,821 incorporated herein by reference. The most simple and most common ring structure is:

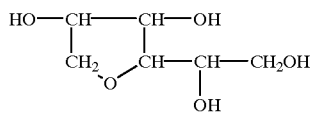

The compound above has four hydroxyl groups present that can be subsequently esterified by the carboxy silicone. There are three classes of materials that we have made "Sorbitan Mono-silicone Esters" wherein one hydroxyl group is reacted, "Sorbitan Di-silicone Esters" wherein two hydroxyl groups are reacted, and "Sorbitan Tri-silicone Esters" wherein three hydroxyl groups are reacted. In a subsequent step, the remaining hydroxyl groups are ethoxylated to make a product that is more water soluble.

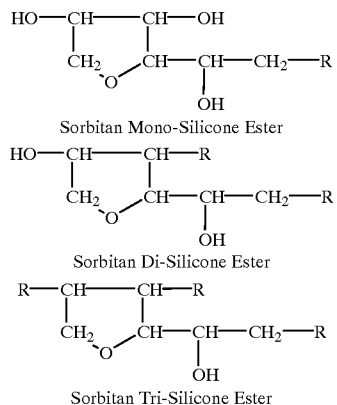

wherein;
R is

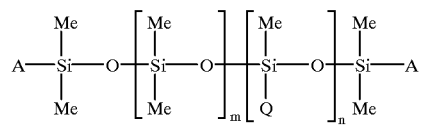

wherein;
Me is methyl;
Q is a —$(CH_2)_c$—C(O)O—;
c is an integer ranging from 3 to 17;
A is either Me—or —Q—
m is an integer ranging from 1 to 200;
n is an integer ranging 0 to 10 when A is —Q—, and an integer ranging from 1 to 10 when A is Me;
x, y and z are each independently integers ranging from 0 to 20 with the proviso that x+y+z be greater than or equal to 1.

Sorbitol Cyclization 995.0 grams of 70% sorbitol in water is placed in a round bottom flask equipped with a condenser to remove water, vacuum and agitation. Nitrogen is applied to exclude air and keep the reaction product light in color. 10.0 grams of 45% KOH is then added. The reaction mass is heated to 100–105 C to remove water. Once the water is removed, the temperature is increased to 180–200 C and one mole of water is distilled off as the material cyclizes.

The resulting product is:

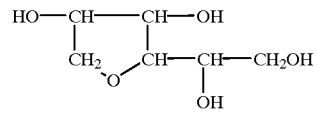

which is used without purification. We refer to this material as sorbitol intermediate. The structure is verified by hydroxyl value, and FTIR.

Ester Synthesis

The esterification reaction is typically carried out using one, two or three equivalents of carboxy silicone. However, intermediate amounts can be used to make products that are mixtures. For example if 2.5 moles of carboxy silicone are used, the resulting product will be a mixture of di and tri ester. The esterification reaction can be carried out with or without catalyst, however when no catalyst is used the reaction times are protracted. Catalysts like benzene sulfonic acid, tin, sulfuric acid, tin salts and the like can be used. The most satisfactory catalyst is stannous oxylate.

General Procedure

To the specified number of grams of carboxy silicone (examples 1–13) is added 165.0 grams of sorbitol intermediate. Next add 0.1% stannous oxylate based upon the total weight of the batch after all ingredients have been charged, under agitation. The temperature of the mass is raised to 180–200 C and water is stripped off as formed. The acid value and hydroxyl value drop to vanishingly small values, and the saponification value increases to theoretical.

The products are clear liquids and are liquid to extraordinary temperatures. They exhibit outstanding lubrication properties and are outstanding viscosity index modifiers.

Example 8

To 609.0 grams of carboxy silicone (examples 1) is added to the sorbitol intermediate. Next add 0.1% stannous oxylate based upon the total weight of the batch after all ingredients have been charged, under agitation. The temperature of the mass is raised to 180–200 C and water is stripped off as formed. The acid value and hydroxyl value drop to vanishingly small values, and the saponification value increases to theoretical.

| Example | Carboxy Example | Silicone Grams |
|---|---|---|
| Sorbitan Mono-Silicone Esters | | |
| 14 | 2 | 1827.0 |
| 15 | 3 | 1051.0 |
| 16 | 4 | 7570.0 |
| 17 | 5 | 2409.0 |
| 18 | 6 | 361.0 |
| 19 | 7 | 3100.0 |
| 20 | 8 | 524.0 |

-continued

| Example | Carboxy Example | Silicone Grams |
|---|---|---|
| 21 | 9 | 290.0 |
| 22 | 10 | 7553.0 |
| 23 | 11 | 2200.0 |
| 24 | 12 | 4000.0 |
| 25 | 13 | 5700.0 |
| Sorbitan Di-Silicone Esters | | |
| 26 | 1 | 1218.0 |
| 27 | 2 | 3654.0 |
| 28 | 3 | 2102.0 |
| 29 | 4 | 15140.0 |
| 30 | 5 | 4818.0 |
| 31 | 6 | 722.0 |
| 32 | 7 | 6200.0 |
| 33 | 8 | 1048.4 |
| 34 | 9 | 580.0 |
| 35 | 10 | 15106.0 |
| 36 | 11 | 4400.0 |
| 37 | 12 | 8000.0 |
| 38 | 13 | 11400.0 |
| Sorbitan Tri-Silicone Esters | | |
| 39 | 1 | 1827.0 |
| 40 | 2 | 5481.0 |
| 41 | 3 | 3153.0 |
| 42 | 4 | 22710.0 |
| 43 | 5 | 7227.0 |
| 44 | 6 | 1083.0 |
| 45 | 7 | 9300.0 |
| 46 | 8 | 1572.0 |
| 47 | 9 | 870.0 |
| 48 | 10 | 22659.0 |
| 49 | 11 | 6600.0 |
| 50 | 12 | 12000.0 |
| 51 | 13 | 17100.0 |

The compouds of the present invention are liquid esters which are outstanding emulsifiers and have no tack on the skin.

What is claimed:

1. A sorbitan mono silicone ester conforming to the following structure:

$$HO-CH-CH-OH$$
$$\phantom{HO-}CH_2\phantom{-}CH-CH-CH_2-R$$
$$\phantom{HO-CH_2\phantom{-}}O\phantom{-CH-}OH$$

wherein;
R is $$A-Si(Me)(Me)-O-[Si(Me)(Me)-O]-[Si(Me)(Q)-O]_m-[Si(Me)(Me)-O]_n-Si(Me)(Me)-A$$

wherein;
Me is methyl;
Q is a —(CH$_2$)$_c$—C(O)O—;
c is an integer ranging from 3 to 17;
A is either Me— or —Q—
m is an integer ranging from 1 to 200;
n is an integer ranging 0 to 10 when A is —Q—, and an integer ranging from 1 to 10 when A is Me.

2. A sorbitan mono silicone ester of claim 1 wherein c is 10.

3. A sorbitan mono silicone ester of claim 1 wherein n is an integer ranging from 2 to 10.

4. A sorbitan mono silicone ester of claim 1 wherein c is 17.

5. A sorbitan mono silicone ester of claim 1 wherein m is 10.

6. A sorbitan di-silicone ester conforming to the following structure:

$$HO-CH-CH---R$$
$$\phantom{HO-}CH_2\phantom{-}CH-CH-CH_2-R$$
$$\phantom{HO-CH_2\phantom{-}}O\phantom{-CH-}OH$$

wherein;
R is $$A-Si(Me)(Me)-O-[Si(Me)(Me)-O]-[Si(Me)(Q)-O]_m-[Si(Me)(Me)-O]_n-Si(Me)(Me)-A$$

wherein
Me is methyl:
Q is a —(CH$_2$)$_c$—C(O)O—;
c is an integer ranging from 3 to 17;
A is either Me— or —Q—
m is an integer ranging from 1 to 200;
n is an integer ranging 0 to 10 when A is —Q—, and an integer ranging from 1 to 10 when A is Me;
x, y and z are each independently integers ranging from 0 to 20 with the proviso that x+y+z be greater than or equal to 1.

7. A sorbitan di-silicone ester of claim 6 wherein c is 10.

8. A sorbitan di-silicone ester of claim 6 wherein n is an interger ranging from 2 to 10.

9. A sorbitan di-silicone ester of claim 6 wherein c is 17.

10. A sorbitan di-silicone ester of claim 6 wherein m is 10.

11. A sorbitan tri-silicone ester conforming to the following structure:

$$R-CH-CH-R$$
$$\phantom{R-}CH_2\phantom{-}CH-CH-CH_2-R$$
$$\phantom{R-CH_2\phantom{-}}O\phantom{-CH-}OH$$

wherein;
R is $$A-Si(Me)(Me)-O-[Si(Me)(Me)-O]-[Si(Me)(Q)-O]_m-[Si(Me)(Me)-O]_n-Si(Me)(Me)-A$$

wherein;
Me is methyl;
Q is a —(CH$_2$)$_c$—C(O)O—;
c is an integer ranging from 3 to 17;
A is either Me— or —Q—
m is an integer ranging from 1 to 200;
n is an integer ranging 0 to 10 when A is —Q—, and an integer ranging from 1 to 10 when A is Me;

x, y and z are each independently integers ranging from 0 to 20 with the proviso that x+y+z be greater than or equal to 1.

12. A sorbitan tri-silicone ester of claim 11 wherein c is 10.

13. A sorbitan tri-silicone ester of claim 11 wherein n is an integer ranging from 2 to 10.

14. A sorbitan tri-silicone ester of claim 11 wherein c is 17.

15. A sorbitan tri-silicone ester of claim 11 wherein m is 10.

* * * * *